(12) United States Patent
Burchardt et al.

(10) Patent No.: US 7,541,149 B1
(45) Date of Patent: Jun. 2, 2009

(54) MONOCLONAL ANTIBODY AND ASSAY FOR DETECTING PIIINP

(75) Inventors: Elmar Reinhold Burchardt, Schwerte (DE); Werner Kroll, Solingen (DE); Mathias Gehrmann, Tönisvorst (DE); Werner Schröder, Wuppertal (DE)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 0 days.

(21) Appl. No.: 09/701,313

(22) PCT Filed: May 17, 1999

(86) PCT No.: PCT/EP99/03392

§ 371 (c)(1),
(2), (4) Date: Nov. 28, 2000

(87) PCT Pub. No.: WO99/61477

PCT Pub. Date: Dec. 2, 1999

(30) Foreign Application Priority Data

May 28, 1998 (EP) .................................. 98109688

(51) Int. Cl.
*G01N 33/53* (2006.01)
*C07K 16/28* (2006.01)
(52) U.S. Cl. ............... 435/7.1; 530/388.24; 530/388.25
(58) Field of Classification Search ........................ None
See application file for complete search history.

(56) References Cited

U.S. PATENT DOCUMENTS

| 4,312,853 | A |   | 1/1982  | Timpl ........................... 424/1   |
| 4,504,587 | A |   | 3/1985  | Timpl et al. .................. 436/538  |
| 5,434,088 | A | * | 7/1995  | Ikeda et al. .................. 436/525  |
| 5,512,283 | A | * | 4/1996  | Byers et al. ............... 424/171.1   |
| 5,679,583 | A |   | 10/1997 | Brocks et al. ............... 436/518    |

FOREIGN PATENT DOCUMENTS

| DE | (11) 63385 | * | 4/1995 |
| EP | 0004940 A1 |   | 10/1979 |
| EP | 0289930 A2 |   | 11/1988 |
| EP | 0298210 A2 |   | 1/1989 |
| EP | 0304292    |   | 2/1989 |
| EP | 0339443 A2 |   | 11/1989 |

OTHER PUBLICATIONS

GenBank accession No. P02461, May 1, 2007, pp. 1-26.*
Lotterer et al. New test for the determination of aminoterminal procollagen-III-peptide in serum using monoclonal antibodies. Journal of Hepatology, 1993, 18(suppl 1):S141, Abstract T-254.*
Xie et al. Production and preliminary application of monoclonal antibodies of Type III procollagen. Mianyixue Zazhi (1994), 10(1), abstract.*

Brocks, D. G., Steinert, C., Gerl, M., Knolle, J., Neubauer, H. P., and Gunzler, V., "A Radioimmunoassay for the N-terminal Propeptide of Rat Procollagen Type III", Matrix, 13:381-387 (1993).
Bulleid, N. J., Wilson, R., and Lees, J. F., "Type-III Procollagen Assembly in Semi-intact Cells: Chain Association, Nucleation and Triple-Helix Folding do not Require Formation of Inter-Chain Disulphide Bonds but Triple-Helix Nucleation Does Require Hydroxylation", Biochem. J., 317: 195-202 (1996).
Colige, A., Li, S. W., Sieron, A. L., Nusgens, B. V., Prockop, D. J., and Lapiere, "cDNA Cloning and Expression of Bovine Procollagen I N-Proteinase: A New Member of the Superfamily of Zinc-Metalloproteinases with Binding Sites for Cells and Other Matrix Components", Proc. Natl. Acad. Sci. USA, 94: 2374-2379 (Mar. 1997).
Davies, B. H., and Madri, J. A., "An Immunohistochemical and Serum ELISA Study of Type I and III Procollagen Aminopropetides in Primary Biliary Cirrhosis", Am. J. Pathol., 128(2): 265-275 (1987).
Eriksen, E. F., Charles, P., Melsen, F., Mosekilde, L., Risteli, L., and Risteli, J., "Serum Markers of Type I Collagen Formation and Degradation in Metabolic Bone Disease: Correlation with Bone Histomorphometry", Journal of Bone and Mineral Research, 8(2): 127-132 (1993).
Fleischmajer, R., Timpl, R., Tuderman, L., Raisher, L., Wiestner, M., Perlish, J. S., and Graves, P. N., "Ultrastructural Identification of Extension Aminopropetides of Type I and III Collagens in Human Skin", Proc. Natl. Acad. Sci. USA, 78(2): 7360-7364 (1981).
Hansen, M., Stoltengerg, M., Host, N. B., Boesby, S., Lorenzen, I., and Bentsen, K. D., "Glucocorticoids Inhibit the Synthesis Rate of Type III Collagen, but do not Affect the Hepatic Clearance of its Aminoterminal Propeptide (PIIINP)", Scand. J. Clin. Lab. Invest., 55: 543-548 (1995).
Hayasaka, A., Koch, J., Schuppan D., Maddrey, W. C., and Hahn, E. G., "The Serum Concentrations of the Aminoterminal Propeptide of Procollagen Type III and the Hepatic Content of mRNA for the α1 Chain of Procollagen Type III in Carbon Tetrachloride-induced Rat Liver Fibrosis", Journal of Hepatology, 13: 328-338 (1991).
Huse, W. D., Sastry, L., Iverson, S. A., Kang, A. S., Alting-Mees, M., Burton, D. R., Benkovic, S. J., and Lerner, R. A., "Generation of a Large Combinatorial Library of the Immunoglobulin Repertoire in Phage Lambda", Science, 246: 1275-1281 (1989).
Jeffers, L. J., Coelho-Little, E., Cheinquer, H., Vargas, C., Civantos, F., Alvarez, L., Reddy, K. R., Parker, T., De Medina, M., Li, X., Hill, M., LaRue, S., and Schliff, E. R., "Procollagen-III Peptide and Chronic Viral C Hepatitis", Am. J. Gastroenterology, 90(9): 1437-1440 (1995).
Kuhn, K., Wiestner, M., Krieg, T., and Muller, P. K., "Structure and Function of the Amino Terminal Propeptide of Type I and III Collagen", Connective Tissue Research, 10: 43-50 (1992).

(Continued)

*Primary Examiner*—Maher M Haddad
(74) *Attorney, Agent, or Firm*—Kevin Stein

(57) ABSTRACT

The present invention relates to monoclonal antibodies binding to the N-terminal procollagen (III) propeptide (PIIINP) molecule which is a proteolytic fragment emanating from the specific cleavage of procollagen (III) by N-proteinase after exocytosis and to an assay using these antibodies.

5 Claims, 4 Drawing Sheets

OTHER PUBLICATIONS

Lee, S.-T., Kessler, E., and Greenspan, D. S., "Analysis of Site-Directed Mutations in Human Pro-α2(1) Collagen Which Block Cleavage by the C-Proteinase", J. Biol. Chem., 265(35): 21992-21996 (1990).

Lees, J. F., and Bulleid, N. J., "The Role of Cysteine Residues in the Folding and Association of the COOH-Terminal Propeptide of Types I and III Procollagen", J. Biol. Chem., 269(39): 24354-24360 (1994).

Moore, G. E., Gerner, R. E., and Franklin, H. A., "Culture of Normal Leukocytes", JAMA, 199(8): 87-92 (1967).

Murawaki, Y., Ikuta, Y., Nishimura, Y., Koda, M., and Kawasaki, H., "Serum Markers for Connective Tissue Turnover in Patients with Chronic Hepatitis B and Chronic Hepatitis C: A Comparative Analysis", Journal of Hepatology, 23: 145-152 (1995).

Niemela, O., Risteli, L., Sotaniemi, E. A., and Risteli, J., "Heterogeneity of the Antigens Related to the Aminoterminal Propeptide of Type III Procollagen in Human Serum", Clinica Chimica Acta, 124: 39-44 (1982).

Peltonen, L., Halila, R., and Ryhanen, L., "Enzymes Converting Procollagens to Collagens", Journal of Cellular Biochemistry, 28: 15-21 (1985).

Plebani, M., and Burlina, A., "Biochemical Markers of Hepatic Fibrosis", Clin. Biochem., 24: 219-239 (1991).

Rohde, H., Bruckner, P., and Timpl, R., "Immunochemical Properties of the Aminopropeptide of Procollagen Type III", Eur. J. Biochem., 135: 197-202 (1983).

Rohde, H., Vargas, L., Hahn, E., Kalbfleisch, H., Brugera, M., and Timpl, R., "Radioimmunoassay for Type III Procollagen Peptide and its Application to Human Liver Disease", European Journal of Clinical Investigation, 9: 451-459 (1979).

Savolainen, E.-R., Goldberg, B., Leo, M. A., Velez, M., and Lieber, C. S., "Diagnostic Value of Serum Procollagen Peptide Measurements in Alcoholic Liver Disease", Alcoholism: Clinical and Experimental Research, 8(4): 384-389 (1984).

Schuppan, D., "Connective Tissue Polypeptides in Serum as Parameters to Monitor Antifibrotic Treatment in Hepatic Fibrogenesis", Journal of Hepatology, 13(3): S17-S25 (1991).

Scott, I. C., Halila, R., Jenkins, J. M., Mehan, S., Apostolou, S., Winqvist, R., Callen, D. F., Prockop, D. J., Peltonen, L., Kadler, K. E., "Molecular Cloning, Expression and Chromosomal Localization of a Human Gene Encoding a 33 kDa Putative Metallopeptidase (PRSM1)", Gene, 174: 135-143 (1996).

Uitto, J., Murray, L. W., Blumberg, B., and Shamban, A., "Biochemistry of Collagen Diseases", Annals of Internal Medicine, 105: 740-756 (1986).

Ristell, J., Nieml, S., Trivedl, P., Mäentausta, O., Mowat, A. P., and Ristell, L., "Rapid Equilibrium Radioimmunoassay for the Amino-Terminal Propeptide of Human Type III Procollagen", Clin. Chem., 34(1): 715:718 (1988).

* cited by examiner

Fig. 2
hP5: Entire cDNA
4.5.2: Mature Monomer
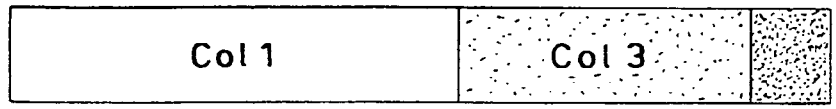
ne6: Deletion Mutant
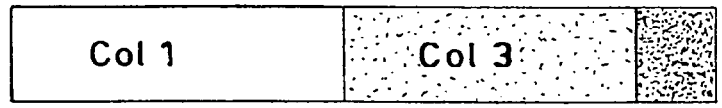
2.8.6: Col 2 Deletion Mutant

MONOCLONAL ANTIBODY AND ASSAY FOR DETECTING PIIINP

STATE OF THE ART

The N-terminal procollagen (III) propeptide (PIIINP) molecule is a proteolytic fragment emanating from the specific cleavage of procollagen (III) by N-proteinase after exocytosis. The present invention relates to antibodies binding to this N-terminal end and to an assay using these antibodies Collagens I and III are synthesized as prepropeptides and are extensively modified posttranslationally. Among the specific intracellular modifications are glycosylations, enzymatic hydroxylation reactions involving lysine and proline in its 3- and 4-positions, and the specific proteolytic removal of the leader peptide. The modified propeptides spontaneously assemble into $[\alpha_1(III)]_3$ homotrimers in the case of collagen (III), and mostly $[\alpha_1(I)]_2\alpha_2(I)$ heterotrimers as well as—to a lesser extent—$[\alpha_1(I)]3$ homodimers in the case of collagen (I) in the microsomal compartments. After exocytosis, the propeptide is first cleaved at the C-terminus of the nascent collagen and then at the N-terminus by a set of specific endoproteases. Remarkably, procollagens I and II are cleaved by a proteinase activity distinct from the N-proteinase activity specific for procollagen (III) (Peltonen et al., 1985). A candidate gene for a human collagen (III)-specific N-proteinase has recently been suggested (Scott et al., 1996). A putative cDNA sequence for bovine procollagen (I) N-proteinase is available (Colige et al., 1996).

PIIINP occurs as a trimer consisting of three identical monomeric PIIINP subunits that are linked by intermolecular disulfide bridges. PIIINP in turn is structurally divided into three domains. The most N-terminally located domain (Col1) consists of a globular structure linked by several intramolecular cystine bridges. Col3 is the intermediate domain and possesses a collagen-like structure characterized by periodic Gly and Pro residues. This domain assembles into a characteristic triple-helical collagen-like structure characterizing the Col3 domain. The Col2 domain encompasses the parts of the procollagen telopeptide region proximal to the N-proteinase cleavage site. The three monomeric PIIINP subunits are assembled as parallel peptide strands in this domain. Characteristically, the Col2 domain contains two cystein residues that are both involved in intermolecular disulfide bridge formation and that are solely responsible for the trimeric structure of PIIINP (Kühn et al., 1982).

The entire cDNA sequence encoding PIIINP was PCR-cloned from a human aorta cDNA library (QUICK-Clone cDNA, Clontech, USA), sequence-verified and subcloned into the bacterial phagemid vector pBluescript SK⁻ (Stratagene, USA). Sequence information has been obtained from the DNASTAR program (Genbank accession # X14420; Ala-Kokko et al., 1989, FIG. 1).

State of the Art

Measurements of Collagen Fragments

Collagen (III) is the characteristic collagen of parenchymal organs and is the second most prevalent collagen in fibrotic tissues. Although collagen (I) is the most prevalent scar-forming collagen and although collagen (I) is upregulated even more drastically in liver fibrosis than collagen (III) it occurs in large amounts in bone (Uitto et al., 1986) and is therefore of limited value in the differential diagnosis of fibrotic processes in parenchymal organs. C-terminal procollagen (I) propeptide serum determinations have therefore been used primarily for the monitoring of disorders of bone metabolism (Eriksen et al., 1993).

Serum levels of the circulating N-terminal procollagen (III) propeptide (PIIINP) are already established as a serum parameter in liver fibrosis patients to estimate the amount of collagen deposition in this organ (e.g. Plebani and Burlina, 1991).

Elevated circulating PIIINP levels may, however, also originate from the cleavage of deposited collagen (III) and thus reflect fibrolysis rather than fibrogenesis (Schuppan, 1991). This is due to the fact that PIIINP is present on the surface of collagen (III) after its deposition in the extracellular matrix (Fleischmajer et al., 1986). The molecular masses of the PIIINP species emanating from fibrolysis seem to be distinct from the species generated in fibrogenesis and include higher as well as lower molecular mass species that circulate in the plasma (Niemela et al., 1982). Although PIIINP serum determinations are fairly well established for the monitoring of liver fibrosis in various underlying diseases such as primary biliary cirrhosis (e.g. Davis and Madri, 1987), chronic hepatitis B and C (Murawaki et al., 1995, Jeffers et al., 1996), and alcoholic liver disease (Savolainen et al., 1984), they are of little help in the establishment of the diagnosis. This is due to two different characteristics of PIIINP serum determinations: 1. circulating PIIINP levels seem to correlate with the acute phase of liver inflammation when excessive collagen deposition is not yet visible histologically and may in fact never become manifest (Savolainen et al., 1984, Hansen et al., 1995) 2. increased circulating PIIINP levels in clinical settings can indicate fibrolysis rather than fibrogenesis because uncleaved PIIINP is present on the surface of collagen (III) fibers and is liberated in the process of collagen degradation (Davis and Madri, 1987).

The diagnostic value of PIIINP determinations has been debated extensively. From molecular sieve experiments with patient sera it has been shown that serum assays recognizing PIIINP detect three different molecular weight forms. The fraction containing lower molecular weight species consists of monomeric Col1 domains. The absolute amount of this circulating Col1 domain is relatively constant in healthy volunteers as well as in patients with chronic active hepatitis and acute alcoholic hepatitis. In addition to the circulating Col1 domain fragment, the antibodies also recognize higher than trimeric PIIINP species in the sera. The exact molecular nature of these high molecular weight species is not known. The relative proportion of the high molecular weight species appears to vary depending on the type of liver disease. Trimeric PIIINP emanating from collagen synthesis and cleaved by N-protease is usually the most abundant PIIINP species but its relative proportion is not constant (Niemela et al., 1982).

An additional problem with the undifferentiated PIIINP serum levels is the unsettled question if PIIINP is correlated with ongoing collagen (III) neosynthesis or whether it is better correlated with manifest collagen deposition in the liver. While some investigators have published that PIIINP levels are best correlated with collagen (III) mRNA (Hayasaka et al., 1991) other studies do not support these observations.

A number of patents have dealt with the problem of PIIINP determinations from patient sera and with methods to improve the diagnostic validity of these determinations. For the measurement of PIIINP in sera of patients with liver diseases several different PIIINP radioimmunoassays have been reported. EP 0004940A1 by Timpl et al., 1979, describes a non-equilibrium inhibition radioimmunoassay based on a bovine antigen-antibody system which shows cross-reactivity with human PIIINP. The procedure disclosed in this patent was subsequently published by Rohde et al., 1979, and was used to develop the RIAgnost PIIIP assay of Behring A G, Marburg, Germany. However, the method does not allow a precise determination of trimeric PIIINP in patient sera since the polyclonal antibodies used in the assay recognize both intact PIIINP and degradation products of PIIINP, in particular the monomeric Col1 domain. In addition, the avidity of the antiserum for the monomeric degradation product is lower than for intact PIIINP. Thus, serum samples show a less steep inhibition curve when compared with the PIIINP standard and the PIIINP concentration has to be estimated by the 50% intercept method which requires three serum dilutions.

In order to overcome the problem with the flat inhibition curve of serum samples an assay variant using antibody Fab-fragments has been developed. The method disclosed in EP 0089008A2 by Timpl et al., 1983, and subsequently published by Rohde et al., 1983, takes advantage of an antiserum that has been generated by immunization of mice with Col1. The antiserum is used to generate antibody Fab-fragments that have an almost equal avidity for Col1 and for intact PIIINP. Therefore, parallel inhibition curves are obtained for serum samples and standards and only a single dilution is required. However, the diagnostic value of this assay is inferior to the RIAgnost PIIIP assay because the Fab-assay does not efficiently differentiate between active and inactive liver diseases.

The low diagnostic value of the Fab-assay has led to the assumption that instead of using an antiserum with equal affinity to PIIINP and Col1, it might be better to use an antiserum which does not recognize Col1 at all. The European patent application EP 0298210A2 by Brocks and Timpl, 1988, describes a method how to raise an antiserum that recognizes intact PIIINP and some undefined procollagen type III species with a higher molecular weight than PIIINP, but not Col1. The antiserum is obtained after immunization of mice with a peptide of defined sequence. However, the peptide claimed is of rat or bovine origin and the antiserum obtained after immunization does not show sufficient cross-reactivity with human PIIINP. Therefore, the assay is not applicable to human samples (Brocks et al., 1993).

Similarly, in European patent application EP 0304292A2 by Risteli and Risteli, 1988, a method is claimed that allows the generation of polyclonal antibodies that have almost no affinity for the PIIINP degradation product Col1. In particular it is claimed that the desired antibodies are obtained after immunization of mice with a trimeric aminoterminal propeptide free from proteolytic enzymes. Moreover, EP 0304292A2 describes an equilibrium RIA which is easier to perform than the non-equilibrium RIAs mentioned in the previous patent applications. A detailed description of the assay, which is commercially available by Orion Diagnostica, Espoo, Finland, was published by Risteli et al., 1988.

The production of two monoclonal antibodies as described in EP 0289930A2 by Brocks et al., 1988, and EP 0339443A2 by Brocks et al., 1989, has allowed the development of an immuno radiometric assay. The reaction pattern of both antibodies against PIIINP separated by gel chromatography is very similar and characterized by the absence of reactivity against Col1. The assay is commercially available as the coated tube RIAgnost PIIIP assay from Behring Diagnostica, Marburg, Germany. The authors also claim the combination of these two antibodies and other unspecified antibodies against PIIINP in sandwich immuno assays.

State of the Art

Recombinant Production of PIIINP

All antibodies described in the literature and in various patents have been raised against PIIINP purified from human or bovine sources. Therefore, the binding epitope of the antibodies is not well characterized.

A number of publications have reported the recombinant production of procollagens. One publication (Lee et al., 1990) claims the production of a collagen $\alpha_2(I)$ mutant in the C-proteinase cleavage site in A2 cells derived from the rat liver epithelial cell line W8 which is deficient for collagen $\alpha_2(I)$. Two recent publications report the recombinant expression of collagen $\alpha_1(III)$ minigenes (Lees and Bulleid, 1994; Bulleid et al., 1996). The sole recombinant expression of the N-terminal procollagen $\alpha_1(III)$ propeptide, e.g. for the purposes of selective immunizations, or the expression of truncated PIIINP, e.g. for the purpose of epitope-mapping, has not been reported. Immunizations have only been carried out with arbitrarily chosen synthetic peptides of uninvestigated secondary structure.

Although immunizations were in our case performed with an oligopeptide that presumably occurred as a monomeric molecule, the resulting antibodies may still preferentially recognize trimeric PIIINP. This may be due to the fact that one antibody can simultaneously bind to two identical epitopes on adjacent chains (Rohde et al., 1983).

A synthetic peptide from the Col1 region (N'-ICESCPfG-GQNYSP-C' (SEQ ID NO: 12)) has been used to raise antibodies that are claimed to be directed against intact PIIINP and that appear not to crossreact with monomeric PIIINP forms (EP 0298210A2 by Brocks and Timpl, 1988). Later, the same authors have published that the antibodies directed against this peptide do not recognize human PIIINP (Brocks et al., 1993).

From the literature cited above it becomes clear that systematic epitope mapping approaches utilizing recombinant DNA technology have not been reported for PIIINP before.

State of the Art

Antibodies Against PIIINP

There is considerable interest in antibodies generated against PIIINP. One source (Rohde et al., 1979) reports the generation of polyclonal antibodies reactive against PIIINP and claims its use as a diagnostic tool for PIIINP determinations in human serum samples. For immunizations, the Col1 domain purified from bovine type III procollagen was used. The results of this investigation were also the subject of EP 000490A1 by Timpl, 1979.

The generation of antibodies against the synthetic oligopeptide fragment (N'-ICESCPTGGQNYSP-C' (SEQ ID NO: 12)) has been the subject of EP 0298210A2 by Brocks and Timpl, 1988. Antibodies recognizing this antigen were claimed to recognize intact PIIINP in rodent sera as well. However, the antibodies were not crossreactive with human PIIINP (Brocks et al., 1993).

EP 0289930 by Brocks et al., 1988, and EP 0339443 by Brocks et al., 1989, claim the generation of two monoclonal antibodies that are selective for the recognition of intact human PIIINP in various body fluids. In particular, they claim the generation of monoclonal antibodies that are directed against an epitope that is not located on Col1 in EP 0289930 and in EP 0339443. While the antibody claimed in EP 0289930 exclusively recognizes higher molecular weight species and intact PIIINP while not reacting with Col1 degradation products, the antibody claimed in EP 0339443 recognizes an additional PIIINP species that is higher in molecular weight than Col1 but smaller than intact PIIINP. The exact nature of the antigen and the basis of this interaction are not further explained. The recognition of a discrete intermediate PIIINP species further underlines the heterogeneity of the circulating PIIINP antigens and emphasizes the need to clearly identify the nature of the epitope that is recognized in each case.

From the available literature it becomes clear that monoclonal antibodies with well defined binding epitopes that recognize human PIIINP have not been reported so far.

The lack of detailed binding information sheds doubts on the diagnostic value of PIIINP determinations using these antibodies.

State of the Art

Monitoring Fibrotic Disease Processes

A diverse array of diseases is associated with the inappropriate or unregulated production of collagen. PIIINP measurements can be performed from patient sera or other body fluids from patients with these diseases. Among these are liver fibrosis of various etiologies, alcoholic cirrhosis, biliary cirrhosis, hepatitis, schistosomiasis, cardiac fibrosis of various etiologies, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, systemic and localized scleroderma, keloids, hypertrophic scars, severe joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, aneurysms of large vessels.

Further fibrotic disorders can be induced or initiated by scar revisions, plastic surgeries, glaucoma, cataract fibrosis, corneal scaring, joint adhesions, graft vs. host disease, tendon surgery, nerve entrapment, Dupuytren's contracture, OB/GYN adhesions, pelvic adhesions, peridural fibrosis, diseases of the thyroid gland or the parathyroids, metastatic bone disease, multiple myeloma, and restenosis.

Early diagnosis is essential for a potential treatment of these diseases. Up to the present, serum tests for fibrotic diseases are not well established and final diagnosis must entirely rely on invasive biopsies.

PIIINP measurements can also be performed to measure the rate of collagen synthesis in patients undergoing therapy with glucocorticosteroids.

Furthermore, the antibodies directed against PIIINP can be used to assess collagen synthesis in tissue samples from patients with fibrotic disease by immunohistochemical staining of kryostat and paraffine sections.

Immunoassay Applications:

The immunoassay of the invention comprises reaction of two antibodies with a human fluid sample, wherein the capture antibody specifically binds to the 30 most N-terminal amino acids of the PIIINP molecule. This capture antibody preferentially binds to trimeric PIIINP. A second antibody of different epitope specificity is used to detect this complex. Preferably the antibodies are monoclonal antibodies and both of said two antibodies of the assay specifically bind to the protein.

The antibody or antibodies of the assay that specifically bind to the PIIINP preferably exhibit less than about 3% cross-reactivity, in an assay such as described in example 6 below or a similar assay with a human plasma sample, with PIIICP, PICP, collagen (III), collagen (I) and collagen (VI).

"Antibody", "antibody of the invention" or other similar term as used herein includes a whole immunoglobulin as well as antigenic binding fragments or immunoreactive fragments which specifically bind to the PIIINP, including Fab, Fab', F(ab')$_2$ and F(v).

The human fluid sample used in the assay of the invention can be any sample that contains the PIIINP, e.g. blood or urine. Typically a serum or plasma sample is employed.

Antibodies of the invention can be prepared by techniques generally known in the art, and are typically generated to a sample of PIIINP. The antibodies can also be generated from an immunogenic peptide that comprises one or more epitopes of the PIIINP that are exhibited by native PIIINP.

More particularly, antibodies can be prepared by immunizing a mammal with a purified sample of PIIINP, or an immunogenic peptide as discussed above, alone or complexed with a capture. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection.

Preferably immunization is done by subcutaneous, intraperitoneal, or intravenous injection. The optimal immunizing interval, immunizing dose, etc. can vary within relatively wide ranges and can be determined empirically based on this disclosure. Typical procedures involve injection of the antigen several times over a number of weeks. Antibodies are collected from serum of the immunized animal by standard techniques and screened to find antibodies specific for PIIINP. Monoclonal antibodies can be produced in cells which produce antibodies and those cells used to generate monoclonal antibodies by using standard fusion techniques for forming hybridoma cells. Typically this involves fusing an antibody-producing cell with an immortal cell line, such as a myeloma cell, to produce the hybrid cell. Alternatively, monoclonal antibodies can be produced from cells by the method of Huse et al. (1989).

One suitable protocol provides for intraperitoneal immunization of a mouse with a composition comprising of purified PIIINP conducted over a period of about two to seven months. Spleen cells then can be removed from the immunized mouse. Sera from the immunized mouse are assayed for titers of antibodies specific for PIIINP prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT) or thymidine kinase deficiency (TK). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. The thus cloned hybridoma is grown in a culture medium, e.g. RPMI-1640 (Moore et al., 1967).

Hybridomas, grown after the fusion procedure, are screened, e.g. by radioimmunoassay or enzyme immunoassay, for secretion of antibodies that bind specifically to PIIIP, e.g. antibodies are selected that bind to the complete PIIINP, to region I of the subsequence but not to region II. Preferably an ELISA is employed for the screen. Hybridomas that show positive results upon such screening can be expanded and cloned by limiting dilution method. Further screens are preferably performed to select antibodies that can bind to PIIINP in solution as well as in human fluid samples.

The assay of the invention is illustrated by the following protocol using alkaline phosphatase as the label of the conjugate antibody. A test sample, e.g. a human serum sample, is added to a PIIINP antibody (i.e., an antibody that binds to the PIIINP) bound on a capture such as a microtiter plate and the antibody-antigen reaction is conducted, followed by addition of the alkaline phosphatase-labeled PIIINP antibody conjugate obtained as outlined above, and then a further antibody-antigen reaction is performed. The antibodies are typically dissolved in solution prior to contact with a test sample. Suitable diluents include those known in the art for use in immunoassays. A specifically preferred solution for dissolving the antibodies for contact with a test sample contains 20 mM Tris, 500 mM sodium chloride, 0.05 mg/ml mouse IgG and 5% (w/v) BSA.

Preferably both the capture and conjugate antibodies of the assay of the invention specifically bind to the PIIINP, and the antibody bound to the support, the human fluid sample and labeled antibody are incubated together, followed by wash steps to remove any unbound labeled antibody and the human plasma sample other than the reacted PIIINP. Suitable washing agents include those known in the art for use in immunoassays. A specifically preferred washing buffer solution contains 27.2 g/l imidazole, 17.5 g/l sodium chloride and 4 ml/l Tween 20. If necessary, a substrate for alkaline phosphatase is added to the assay and the reaction products are assayed for enzyme activity by measuring the absorbance or fluorescence of the resulting product. The detected amount of bound labeled antibody is directly proportional to the concentration of PIIINP in the assayed human serum sample. Thus a quantitative determination of the PIIINP concentration in the plasma test sample can be determined by comparison of the absorbance or fluorescence of the test sample with absorbance values obtained from standardized solutions that contain known amounts of PIIINP. It may be desirable to prepare calibration curves from absorbance values obtained from a number of standardized solutions to facilitate interpretation of values obtained from a test sample.

A specifically preferred immunoassay of the invention was conducted as follows. The capture monoclonal antibody and conjugate monoclonal antibody labeled with alkaline phosphatase (AP) was incubated together with a human plasma sample at 37° C. for 30 minutes. The plate was then washed and incubated for 15 minutes at room temperature with AP substrate and the bound conjugate was quantitated.

PIIINP can be purified from a human serum sample by use of capture complexes coupled with one or more antibodies of the invention in sufficient quantities for immunization. Sufficient amounts were purified and hence the invention includes methods for obtaining purified PIIINP using the antibodies of the invention and related apparatus. A suitable purification procedure provides coupling an antibody of the invention on an appropriate capture as is known in the art, such as a gel or resin, then packing the capture in a column, and then eluting a sample solution containing PIIINP through the column to selectively adsorb PIIINP. The antibody can be suitably coupled onto the capture by known methods, e.g. the cyanogen bromide method, glutaraldehyde method, aqueous carbodiimide method, active ester method, and the like. The antibody also may be physically adsorbed on the surface of the capture.

EXAMPLE 1

Production of Recombinant PIIINP

Cloning of PIIINP cDNA

PCR was carried out following the manufacturer's recommendations for buffer conditions with 2.5 units of Taq polymerase (Boehringer Mannheim, Germany). Two specific primers with KpnI and HindIII restriction sites integrated at their respective 5' ends (P1 and P5, table 1) were added to a final concentration of 500 µM each. 1 µl of QUICK-Clone cDNA from human aorta was used as a template in a 100 µl PCR reaction. PCR was carried out with a high performance UNO thermocycler manufactured by Biometra, Germany. The following program was used: initial template denaturation step: 5 min at 94° C. Standard cycle conditions were: 45 sec at 94° C., 60 sec at 55° C., 60 sec at 72° C. 30 Cycles were carried out. A 420 sec extension step completed the program. The resulting PCR fragment was purified from a 2% agarose gel with a QIAEX II gel extraction kit (Qiagen, Germany) and phosphorylated by T4 polynucleotide kinase treatment (Boehringer Mannheim, Germany). The acterial phagemid vector pBluescript SK⁻ was digested with the restriction enzyme SmaI (Boehringer Mannheim, Germany), and the linearized plasmid was dephosphorylated with calf intestine phosphatase from Boehringer Mannheim, Germany. The enzymatically modified PCR fragment and the vector were ligated with T4 ligase (Boehringer Mannheim, Germany) for 12 h at 16° C. All enzymatic modification steps were carried out according to the manufacturer's recommendations. The ligated plasmid was transformed into the $E.$ $coli$ strain sure II (Stratagene, USA) according to the procedure described in Sambrook et al., 1988. The resulting colonies were expanded in LB medium with 100 µg/ml Ampicillin and the plasmid DNA was isolated according to the Qiagen Mini Kit protocol (Qiagen, Germany). The plasmid was tested for the integration of the insert by digestion with KpnI and HindIII (Boehringer Mannheim, Germany) according to the manufacturer's recommendations. A positive clone (hP5) was identified. The clone was expanded, sequence-verified by two-directional nucleotide sequencing in an Applied Biosystems (USA) sequencer, and larger quantities of the hP5 plasmid were isolated. It served as a template for all expression constructs described below.

Subsequently, the plasmid hP5 served as a template for the generation of an N-terminal His tag expression construct encompassing the entire propeptide region but lacking the N-terminally located presequence and the telopeptide region distal to the N-proteinase cleavage site. To this end, 1 µg of the hP5 plasmid was used as the template and the amplification was carried out with the primers P3 and P14 (see table 1 for sequence information). P3 and P14 contained KpnI and HindIII restriction sites at their ends, respectively. 12 PCR cycles were carried out under the same cycle conditions as described above. This PCR product was blunt-endedly subcloned into the phagemid vector pBluescript SK⁻. A plasmid containing the cDNA of mature PIIINP was obtained and designated 4.5. This plasmid was digested with KpnI and HindIII (Boehringer Mannheim Germany) and the PIIINP cDNA was purified from a 2% agarose gel. The insert was subsequently phosphorylated. It was ligated with the His tag expression plasmid pQE30 (Qiagen, Germany) that had previously been digested with the same set of restriction enzymes as the insert, and dephosphorylated. Competent *E. coli* sure II were transformed with the plasmid. A colony carrying the pQE30 derivative with the PIIINP sequence was identified and expanded. All modification steps were carried out in anology to the procedure outlined for the generation of hP5. The clone was designated 4.5.2.

Expression and Purification of the Recombinant N-Terminal His Tag PIIINP Fusion Protein and Generation of N- and C-Terminally Truncated Mutants Briefly, after a second transformation, the corresponding N-terminal His tag fusion protein was expressed in the *E. coli* strain M15 carrying the pREP4 plasmid (according to the QIAexpressionist manual, p. 35, Qiagen, Germany, incubation temperature 37° C.). The recombinant fusion protein was purified over a Ni-NTA Superflow column (Qiagen, Germany) according to the purification protocol from the manufacturer (Protocol 7, QIAexpressionist manual, pp. 45-46, Qiagen, Germany).

For the generation of an N-terminally truncated protein, a primer recognizing a sequence downstream of the sequence coding for the first 30 N-terminal amino acids of PIIINP (P11-2, table 1) was used in combination with a primer specific for the sequence encompassing the C-terminally located N-proteinase cleavage site (P14, table 1). The experimental procedures were completely analogous to the those described for the construction of the plasmid 4.5.2 except that the insert was subcloned into the pQE31 expression vector (Qiagen, Germany) and that the upstream primer (P11-2) contained a PstI restriction site at its 5' end. Therefore, the insert and the vector were digested with PstI (Boehringer Mannheim, Germany) rather than KpnI. This construct was designated clone6. After induction with IPTG an N-terminal fusion protein lacking the first 30 amino acids from the Col1 domain of PIIINP and differing from the 4.5.2-derived peptide in the amino acid sequence adjacent to the N-terminal His tag amino acid sequence was purified over a Ni-NTA column.

Another truncated PIIINP cDNA sequence was generated by PCR using a primer pair recognizing the sequence coding for the N-terminal end of the molecule (P3, table 1) and the sequence just upstream of the sequence coding for the entire Col2 domain (P12, table 1). After subcloning this fragment into the pQE30 expression vector, transformation, expression of the recombinant protein and its purification, a truncated PIIINP lacking 21 amino acids at its C-terminus when compared to the non-truncated molecule was obtained. The construct was designated 2.8.6. Again, all experimental procedures were carried out in analogy to the ones described for the preparation of the 4.5.2 plasmid.

Multimerization Attempts with rhPIIINP

The purified proteins were separated by electrophoresis on a 12.5% SDS gel (Sambrook et al., 1989). To determine which molecular weight disulfide-linked PIIINP species and truncated mutants were recombinantly expressed in the strain M15 with the pREP4 plasmid, mercaptoethanol [5% (v/v)] as the reducing agent was omitted from the sample buffers and the resulting bands were compared with a molecular size standard and with their mercaptoethanol-reduced counterparts.

By comparison of the unreduced PIIINP species with the reduced protein, that appeared as one band on an SDS gel, it became apparent that the recombinant PIIINP was largely synthesized as a monomeric protein. Only species with electrophoretic mobilities corresponding to monomers were discernable in each case (FIG. 3).

Amino Acid Sequencing of the Purified Recombinant Proteins

Sample preparation of PIIINP to remove buffer and other contaminants was performed using the ProSpin sample preparation cartridge from Applied Biosystems (USA) and Centricon concentrators (Amicon, USA), by blotting onto PVDF-membrane after SDS-gel electrophoresis or by gel filtration in formic acid on a silica gel column. A vertical electrophoresis unit (LKB/Pharmacia, Germany), a trans blot cell and a power supply for blotting model 250/2.5 (BioRad, Germany) were used. The reagents for electrophoresis and the PVDF-membrane were from BioRad. All other chemicals used were of pro analysis or biochemical grade (Merck, Germany). The prestained protein marker was from BioRad (Germany).

N-terminal sequence analyses of PIIINP-fragments were performed using the gas-liquid-solid-phase protein sequencer 473A from Applied Biosystems. The standard sequencer program was used. The sequencer, the different running programs, the cycles, as well as the PTH-separation system, are described in detail in the respective manual (User's manual protein sequencing system model 473A (1989), Applied Biosystems, USA). The detection of PTH-amino acids was performed on-line using an RP-18-column (220 mm×2 mm, 5μ-material) PTH-column from Applied Biosystems. The PTH-amino acids were identified and quantified by a 50 pM standard of all PTH-amino acids. The data were collected and integrated using the sequencer data system 610A from Applied Biosystems. About 20 ng of the respective PIIINP fragments was used for sequencing.

The 4.5.2, 2.8.6, and clone6 proteins were N-terminally sequenced as described above. The number of cycles was sufficient in each case to reach the collagen sequence of the fusion protein. Table 2 summarizes the results from the amino acid sequencing of three representative PIIINP proteins. It was identical to the published sequence in each case.

EXAMPLE 2

Immunization

BALB/c female mice were immunized with PIIINP to provide spleen donors for the PEG fusion, disclosed below, that generated monoclonal antibodies that specifically bind to PIIINP.

BALB/c female mice were sensitized with 10 µg each of purified PIIINP in immunogen emulsion prepared as follows:

0.125 ml procollagen-III-N-terminal-propeptide (325 µg/ml in 50 mM Tris/50 mM NaCl/0.1 mM EDTA pH 7.4)

1.500 ml Complete Freund's Adjuvant 1.375 ml Dulbecco's Phosphate Buffered Saline Each mouse was injected with 0.5 ml of this immunogen emulsion i.p. The mice were boosted with doses of up to 50 µg of purified PIIINP i.p. in an immunization protocol that was carried out for approximately six months.

EXAMPLE 3

ELISA Assay for PIIINP Antibodies

Coating Microtiter Plates with PIIINP

PIIINP was diluted in a coating buffer (carbonate buffer, pH9) at a concentration of 1 µg/ml. 100 µl of each solution (10 ng PIIINP) were placed in each well of the microtiter plates, which were sealed and incubated overnight at 2-8° C. The contents of the wells were then aspirated and the plates were washed once with wash/storage buffer, the wash aspirated, and the plates again resealed. The plates were stored at 2-8° C. until use.

EXAMPLE 4

Preparation of Hybridomas

Hybridomas secreting monoclonal antibodies to procollagen-III-N-terminal-propeptide were generated by two cell fusions. The PEG fusion technique was employed. The myeloma cells used were HRPT-minus P3-X63-Ag8.653 (P3X) (ATCC CRL1580). Selection for hybrids was accomplished using HAT media (hypoxanthine, aminopterin and thymidine). Unfused P3X myeloma cells will not survive in this medium as they lack the apparatus to use hypoxanthine to produce purines. The aminopterin present in the medium blocks the endogenous synthesis of purines and pyrimidines.

Fusion to Form Hybridoma Procollagen-III-N-Terminal-Propeptide

Splenocyte Preparation

Spleen cells were obtained from a mouse immunized with procollagen-III-N-terminal-propeptide as described for Example 1. The cells were released from the spleen using a forceps and needle, then suspended in 12 ml of cold 20% Complete Medium without serum (RPMI 1640 base, Gibco). The cells were then centrifuged at 200 g for 10 minutes after which the supernatant was removed by aspiration, and the cells were resuspended again in cold medium. This washing process was repeated twice, and the cells resuspended in a final volume of 10 ml. The viable cell count of the splenocytes was $1.7 \times 10^8$ at a viability of 98% by Trypan Blue exclusion technique.

Myeloma Preparation

The myeloma cells were harvested mechanically, pooled, and centrifuged at 200 g for 10 minutes after which the supernatant was removed by aspiration, and the cells were resuspended in 50 ml of 20% Complete Medium. The viable cell count of the myeloma cells was $2.9 \times 10^6$ viable cells per ml at a viability of 76%.

Fusion of the Splenocytes and Myeloma Cells

The splenocytes and 15 ml of the myeloma cell suspension were combined at a spleen cell to myeloma cell ratio of approximately 4:1 with a total viable cell count of $2.13 \times 10^8$. The volume was brought up to 50 ml with cold 20% Complete Medium without serum and the cells then centrifuged at 200 g for 10 minutes. The cell pellet was then washed twice with this medium at a volume of 50 ml. After the final wash, the supernatant was removed by aspiration and the pellet centrifuged at 200 g for 3 minutes and the remaining supernatant aspirated. The cells were then fused with 40% PEG (molecular weight 7,000 to 9,000) buffered in RPMI 1640; fusion was performed in a tube held in a warm (37° C.) water bath. 1 ml of PEG solution warmed to 37° C. was added to the pellet and incubated for 1 minute. The PEG solution was then diluted by addition of 20 ml of warm 20% Complete Medium without serum. The flused cells were incubated at 37° C. for 10 minutes and then centrifuged at 200 g for 10 minutes.

The flused cell pellet was then resuspended in 50 ml of 20% Complete Medium and plated at cell densities of $1.09 \times 10^5$ to $4.26 \times 10^5$ per well. The cells were plated in a final volume of 200 µl per well of 20% Complete Medium with 250 units/ml IL-6. After overnight incubation at 37° C. and 10% $CO_2$, one half of the medium in each well was aspirated and the cells were fed with 20% HAT, 20% HAT with 5 µg/ml STM or 20% HAT with 500 units/ml IL-6. The cells were visually scanned and fed periodically with these media for several weeks, while the growth of the hybridomas was monitored and growing wells were screened for the presence of anti-PIIINP antibodies beginning at day 12 to 14 post-fusion using the previously described PIIINP-coated microtiter plates and standard methods well known to the biochemical experts.

EXAMPLE 5

Application of Recombinant PIIINP and of the Truncated PIIINP Peptides for the Characterization of the Epitope-Specificity of Monoclonal Anti-bodies Raised Against Recombinant PIIINP Principle To screen for epitope-specific monoclonal antibodies, all three recombinant peptides were used. Those monoclonal antibodies recognizing all three peptides were not used any further because these antibodies were either directed against the N-terminal His tag or against the region between the very N-terminal epitopes of Col1 and the beginning of Col2. Antibodies recognizing only the complete peptide (4.5.2) and the C-terminal deletion peptide (2.8.6) lacking the 21 most C-terminal amino acids corresponding to a deletion of the entire Col2 domain and not reacting with the N-terminal deletion peptide (clone6) lacking the 30 most N-terminally located amino acids were classified as epitope-specific for the N-terminal Col1 region. FIG. 2 shows the epitopes present on all PIIINP constructs and table 4 summarizes the results from ELISA and Western blot assays obtained with the different antibodies and antigens.

By the same token, antibodies recognizing only the complete peptide (4.5.2) and the N-terminal deletion peptide (clone6) were identified as epitope-specific for the C-terminally located Col2 domain.

To characterize the binding characteristics of the newly generated monoclonal antibodies, both ELISA and Western Blot techniques were applied. Two suitable monoclonal antibodies (mAb 35J22 and mAb 35J23) that exclusively recognized the 30 most N-terminal amino acids of PIIINP as their binding epitopes and that allowed the sensitive detection of native PIIINP from patient samples were selected. The cell line from which the mAb 35J22 monoclonal antibody was produced was deposited with the American Type Culture Collection (ATTC) Patent Depository (10801 University Blvd., Manassas, Va. 20110-2209, USA) on Oct. 14, 2008 under the provisions of the Budapest Treaty for the International Recognition of the Deposit of Microorganisms for the Purpose of Patent Procedure. The deposit was made under the Identification Reference "Murine Hybridoma 35J22" and the ATCC has assigned the deposited cells ATCC accession number PTA-9545.

1. ELISA:

After identification of the optimal titer using complete recombinant PIIINP in an ELISA assay where the recombinant PIIINP was coated at a fixed mass concentration, the deletion peptides were coated at the same concentration, and the signal intensity was determined in exact analogy to the complete PIIINP. Table 4 summarizes the results of this ELISA assay for the monoclonal antibody 35J23 and recognition of the different antigens.

2. Western Blot:

After determination of the optimal titers of the different antibodies all three PIIINP variants were electrophorized in equal molar concentrations and Western Blots were performed. Differences in antigen recognition could thus be correlated with epitope-specificity.

EXAMPLE 6

Immunization with an Oligopeptide to Raise Antibodies that are Selective for the Col2 Domain In order to raise antibodies selective for the Col2 domain an oligopeptide sequence corresponding to the 21 amino acids located immediately N-terminal to the N-proteinase cleavage site was chosen. The exact sequence of the peptide is given in table 3. The last 14 amino acids of the oligopeptide sequence are identical to the sequence of the Col2 domain of PIIINP. As the binding epitope of a typical monoclonal antibody is at least 6 amino acids, antibodies raised against this oligopeptide typically recognize a subsequence of the Col2 region.

A monoclonal antibody, mAb 35JC2 was raised and further characterized.

EXAMPLE 7

Establishment of a PIIINP Immunoassay Based on the Recognition of Two Complementary Epitopes of the PIIINP Molecule by Two Different Monoclonal Antibodies Measurements of the N-terminal procollagen (III) propeptide (PIIINP) concentrations in patients' sera were carried out employing the sandwich technology. An epitope-specific monoclonal antibody recognizing an N-terminal epitope of the PIIINP molecule (mAb 35J23) specifically bound and immobilized the circulating serum PIIINP. A second monoclonal antibody (mAb JC2) was used to detect this complex.

The combination of the site-specific monoclonal antibodies as described above exclusively recognized higher molecular weight species of PIIINP that are related to the de novo deposition of procollagen (III) in the extracellular matrix in the sera of all patients and controls. This specificity for intact PIIINP further distinguishes the novel assay from assays that additionally recognize lower molecular weight species. Shorter PIIINP fragments probably represent degradation products emanating from PIIINP and may not necessarily reflect recent collagen synthesis. Therefore, the new assay described above is very specific for the purpose of monitoring collagen synthesis versus collagen breakdown.

EXAMPLE 8

Establishment of a PIIINP Immunoassay Based on the Capture of the PIIINP Molecule by a Monoclonal Antibody and Detection of this Complex with Polyclonal Antiserum A microtiter plate (Nunc Maxisorb, Germany) was coated with mAb 35J23 or mAb 35J22 (2 µg/ml, total volume per well 100 µl) overnight at 4° C. On the following day the supernatant was discarded and the wells were blocked with 3% BSA (w/v) in PBS (total volume per well 200 µl) for 2 h. The wells were washed 3× with washing buffer (0.05% Tween 20, BioRad, Germany). Subsequently, 50 µl of patient serum was applied to each well for 1 h. The serum was removed from the wells and the plates were washed 3× with washing buffer as described above. The polyclonal anti-PIIINP antiserum from Biodesign (UK, lot # 40331R) was used to detect this complex (dilution 1:500 (v/v), total volume per well 100 µl). After 3× washing, the peroxidase-labeled anti-rabbit antibody A 0545 from Sigma (Germany) was applied (dilution 1:20,000 (v/v), total volume per well 100 µl). After 5× washing the ELISA assay was developed with 100 µl of TMB peroxidase substrate+peroxidase solution B (1:1 (v/v), both from Kirkegaard & Perry Laboratories, USA) for 30 min. The reaction was stopped by the addition of 100 µl of 1 $NH_2SO_4$ and the O.D.'s were determined at 450 nm.

Most surprisingly, both monoclonal antibodies, mAb 35J22 and mAb 35J23, preferentially bound to trimeric PIIINP vs. the monomeric recombinant protein 4.5.2.

EXAMPLE 9

PIIINP Assay on an Automated Immunoanalyzer

FIG. 3 and table 4 show the correlation of the O.D.'s obtained with this assay with the PIIINP concentrations determined with the Orion RIA when samples from the same selected patients were measured with both methods.

The calibration curve shown in FIG. 4 was obtained with recombinant PIIINP when tested with the ELISA assay described in Example 8. The assay was performed as described above for patient sera, except that successive dilutions of recombinant PIIINP were coated (total volume 100 µl). The titer of the polyclonal anti-PIIINP antiserum was varied in this experiment. Best results were obtained with 1:500 dilutions of the anti-PIIINP antiserum. When the results are compared to the measurements from patient sera with known PIIINP concentrations it becomes clear that this type of assay preferentially recognizes intact PIIINP while not avidly recognizing monomeric recombinant material. With the recombinant antigen the detection threshold was approximately 100 ng/ml and the dynamic range of the assay was shifted to PIIINP concentrations 20-100 times higher than with the trimeric material in patient sera. Notably, the preferential recognition of the trimeric material is not due to the polyclonal antiserum that does not discriminate between monomeric and trimeric material as has been shown in simple ELISA assays performed with only the polyclonal antiserum (data not shown).

Table 5 shows the PIIINP concentrations in the sera from patients with Child-classified fibrotic liver disease. The data imply a correlation between circulating PIIINP levels as determined with the sandwich immuno assay described above and the clinical severity of the fibrotic liver disease.

The PIIINP assay was set up as a sandwich immunoassay with simultaneous addition of both antibody reagents and sample, and late addition of magnetic particles.

- 10 µl serum sample and 10 µl of magnetic particle buffer were pipetted into the reaction cuvette.
- 30 sec. later 65 µl reagent R1 and 65 µl reagent R2 were dispensed into the cuvette. Reagent R1 contains a fluoresceinated monoclonal anti-PIIINP anti-body in a buffered solution. Reagent R2 contains an anti-PIIINP antibody of different epitope-specificity conjugated to alkaline phosphatase in a buffered solution.
- The reaction mixture was incubated for 21 min at 37° C. to form the sandwich immune complex.
- 10 µl of magnetic particles coated with an anti-fluorescein antibody were added, and the mixture was incubated at 37° C. for additional 8 min.
- The immune complex bound to the particles was separated from the reaction mixture by applying an external magnetic field. The particles were washed to remove excess sample and reagent.

300 μl p-nitrophenolate was added to the reaction mixture. The colored p-nitrophenolate anion was formed, and the rate of formation was directly proportional to the PIIINP concentration present in the sample. At low concentrations the rate of absorbance increase was monitored at 405 nm, at high color formation rate the filter wavelength was switched to 450 nm.

LITERATURE

Brocks D, Günzler-Pukall V, Hachniann H, Pünter J, and Timpl R (1989) Monoklonaler Antikörper zur selektiven immunologischen Bestimmung von intaktem Prokollagen Peptid (Typ III) und Prokoliagen (Typ III) in Körperflüssigkeiten. European Patent Appl. 0339443A2

Brocks D and Timpl R (1988) Verfahren zur selektiven immunologischen Bestimmung von intaktem Prokollagen Peptid (Typ III) und Prokollagen (Typ III) in Körperflüssigkeiten und Mittel zu dessen Durchführung. European Patent Appl. 0298210A2

Brocks D, Pünter J, Strecker H, and Timpl R (1988) Monoklonaler Antikörper zur selektiven immunologischen Bestimmung von intaktem Prokollagen Peptid (Typ III) und Prokollagen (Typ III) in Körperflüssigkeiten. European Patent Appl. 0289930A2

Brocks D G, Steinert C, Gerl M, Knolle J, Neubauer H P, and Günzler V (1993) A radioimmunoassay for the N-terminal propeptide of rat procollagen type (III). Matrix 13: 381-387

Bulleid N J, Wilson R, and Lees J F (1996) Type-III procollagen assembly in semi-intact cells: chain association, nucleation and triple-helix folding do not require formation of inter-chain disulfide bonds but triple-helix nucleation does require hydroxylation. Biochem. J. 317: 195-202

Colige A, Nusgens B V, and Lapiere C M (1996) Cloning of the cDNA of the bovine procollagen I N-proteinase. Genbank accession number X96389

Davis B H and Madri J A (1987) An immunohistochemical and serum ELISA study of type I and III procollagen aminopeptides in primary biliary cirrhosis. Am. J. Path. 128: 265-275

Eriksen E F, Charles P, Melsen F, Mosekilde L, Risteli L, and Risteli J (1993) Serum markers of type I collagen formation and degradation in metabolic bone disease: Correlations to bone histomorphometry. J. Bone Miner. Res. 8: 127-132

Fleischmajer R, Timpl R, Tudermann L, Raisher L, Wiestner M, Perlish J S, and Graves P N (1981) Ultrastructural identification of extension aminopropetides of type I and III collagens in human skin. Proc. Natl. Acad. Sci. USA 78: 7360-7364

Hansen M, Stoltenberg M, Host N B, Boesby S, Lorenzen I, and Bentsen K D (1995) Glucocorticoids inhibit the synthesis rate of type III collagen, but do not affect the hepatic clearance of its aminoterminal propeptide (PIIINP). Scand. J. Lab. Invest. 55: 543-548

Hayasaka A, Koch J, Schuppan D, Maddrey W C, and Hahn E G (1991) The serum concentrations of the aminoterminal propeptide of procollagen type III and the hepatic content of mRNA for the $\alpha 1$ chain of procollagen type III in carbon tetrachloride-induced rat liver fibrogenesis. J. Hepatology 13: 328-338

Huse W D, Sastry L, Iverson S A, Kang A S, Alting-Mees M, Burton D R, Benkovic S J, and Lerner R A (1989) Generation of a large combinatorial library of the immuno-globulin repertoire in phage lambda. Science 246: 1275-1281

Jeffers L J, Coelho-Little M E, Chemquer H, Vargas C, Civantos F, Alvarez L, Reddy R, Parker T, de Medina M, Li Y, Hill M, LaRue S, and Schiff E R (1996) Procollagen-III-peptide and chronic viral C hepatitis. Am. J. Gastroent. 90: 1437-1440

Kühn K, Wiestner M, Krieg T, and Müller P K (1982) Structure and function of the amino terminal propeptide of type I and III collagen. Conn. Tissue Res. 10: 43-50

Lee S T, Kessler E, and Greenspan D S (1990) Analysis of site-directed mutations in human pro-$\alpha_2$(I) collagen which block cleavage by the C-proteinase. J. Biol. Chem. 265: 21992-21996

Lees J F and Bulleid N J (1994) The role of cysteine residues in the folding and association of the COOH-terminal propeptide of types I and III procollagen. J. Biol. Chem. 269: 24354-24360

Moore G E, Gerner R E, and Franklin H A (1967) Culture of normal human leukocytes. JAMA 199: 87-92

Murawaki Y, Ikuta Y, Nishimura Y, Koda M, and Kawasaki H (1995) Serum markers for connective tissue turnover in patients with chronic hepatitis B and chronic hepatitis C: A comparative analysis. J. Hepatol. 23: 145-152

Niemelä O, Risteli L, Sotaniemi E A, and Risteli J (1982) Heterogeneity of the antigens related to the aminoterminal propeptide of type III procollagen in human serum. Clinica Chimica Acta 124: 39-44

Peltonen L, Halila R, and Ryhänen L (1985) Enzymes converting procollagens to collagens. J. Cell. Biochem. 28: 15-21

Plebani M and Burlina A (1991) Biochemical markers of hepatic fibrosis. Clin. Biochem. 24: 219-239

Risteli J and Risteli L (1988) Antibody to propeptide of procollagen type III, and assay method using it. European Patent Appl. 0304292A2

Rohde H, Bruckner P, and Timpl R (1983) Immunochemical properties of the aminopropeptide of procollagen type III. Eur. J. Biochem. 135: 197-202

Rohde H, Vargas L, Hahn E, Kalbfleisch H, Bruguera M, and Timpl R (1979) Radioimmunoassay for type III procollagen peptide and its application to human liver disease. Eur. J. Clin. Invest. 9: 451-459

Savolainen E R, Goldberg B, Leo M A, Velez M, and Lieber C S (1984) Diagnostic value of serum procollagen peptide measurements in alcoholic liver disease. Alcohol. Clin. Exp. Res. 8: 384-389

Schuppan D (1991) Connective tissue polypeptides in serum as parameters to monitor antifibrotic treatment in hepatic fibrogenesis. J. Hepatology 13 (Suppl. 3): S17-S25

Scott I C, Halila R, Jenkins J M, Mehan S, Apostolu S, Winqvist R, Callen D F, Prockop D J, Peltonen L, and Kadler K E (1996) Molecular cloning, expression and chromosomal localization of a human gene encoding a 33 kDa putative metallopeptidase (PRSM1). Gene 174: 135-143

Timpl R (1979) Verfahren zur radioimmunologischen Bestimmung von Prokollagen (Typ III) und Prokollagen-Peptid (Typ III), zur Herstellung von für das Verfahren geeignetem Prokollagen-Peptid (Typ III) und zur Herstellung von Anti-Prokollagen-Peptid (Typ III)-Serum. European Patent Appl. 000490A1

Timpl R, Brocks D, Neubauer H, and Strecker H (1983) Verfahren zur gemeinsamen immunologischen Bestimmung von Prokollagen-Peptid (Typ III) und Prokollagen-Peptid Col1 (Typ III) und Verfahren zur Herstellung von Anti-Prokollagen-Peptid Col1 (Typ III)-Serum. European Patent Appl. 0089008A2

Uitto J, Murray L W, Blumberg B, and Shamban A (1986) Biochemistry of collagen in diseases. Ann. Int. Med. 105: 740-756

TABLES

TABLE 1

Primer Sequences hP5 (template extending from secretion sequence to telopeptide region)
P1 and P5
P1:   5'-CGCG GGT ACC AAG GGG AGC TGG CTA CTT CTC-3'   (SEQ ID NO:3)
P5:   5'-CGCG AAG CTT AGG ATA GCC TGC GAG TCC TCC-3'   (SEQ ID NO:7)

4.5.2 (entire cDNA sequence)
P3 and P14
P3:    5'-CGCG GGT ACC CAG GAA GCT GTT GAA GGA GGA-3'  (SEQ ID NO:6)
P14:   5'-CGCG AAG CTT GGG AGA ATA GTT CTG AGG AC-3'   (SEQ ID NO:13)

Clone6 (N-terminal deletion of 30 aa C-terminally adjacent to
secretion leader sequence)
P11-2 and P14
P11-2: 5'-CGCG CTG CAG TGT GAC TCA GGA TCC GTT CT-3'   (SEQ ID NO:4)
P14:   5'-CGCG AAG CTT GGG AGA ATA GTT CTG AGG AC-3'   (SEQ ID NO:13)

2.8.6 (C-terminal deletion of 21 aa N-terminally adjacent to
N-proteinase cleavage site)
P3 and P12
P3:    5'-CGCG GGT ACC CAG GAA GCT GTT GAA GGA GGA-3'  (SEQ ID NO:6)
P12:   5'-CGCG AAG CTT AGG GGA CCC TGG TTG TCC T-3'    (SEQ ID NO:5)

TABLE 2

| | |
|---|---|
| PIIINP 4.5.2 Met-Arg-Gly-Ser-His-His-His-His-His-His-Gly-Ser-Ala-Cys-Glu-Leu-Gly-Thr-Gln-Glu-Ala-Val-Glu-Gly-Gly-... | (SEQ ID NO:8) |
| PIIINP 2.8.6 Met-Arg-Gly-Ser-His-His-His-His-His-His-Gly-Ser-(Ala)-(Cys)-Glu-Leu-Gly-Thr-Gln-Glu-Ala-(Val)-Glu-Gly-... | (SEQ ID NO:9) |
| PIIINP clone6 Met-Arg-Gly-Ser-His-His-His-His-His-His-Thr-Asp-Pro-His-Ala-Ser-Ser-Val-Pro-Arg-Val-Asp-Leu-Gln-... | (SEQ ID NO:10) |

TABLE 3

| Antigen | Antibodies mAb 35J23 and mAb 35J22 directed against N-terminal epitope [Reactivity] | Antibody 35JC2 directed against C-terminal epitope [Reactivity] |
|---|---|---|
| 4.5.2 (intact PIIINP with 6xHis tag) | +++ | +++ |
| PIIICP4.1 (unrelated antigen with identical His tag sequence) | − | − |
| 2.8.6 (21 aa C-terminal deletion protein) | +++ | − |
| clone6 (30 aa N-terminal deletion protein) | − | +++ |

Table 3 summarizes the results from ELISA assays measuring the reactivity of the two monoclonal antibodies against recombinant 4.5.2 and against the deletion proteins. The N-terminal amino acid sequences were identical in all cases up to the beginning of the collagen sequence. The control protein, PIIICP4.1, was an N-terminal 6xHis tag fusion protein identical to the PIIINP proteins in its N-terminal non-collagen-sequence and was used to ascertain that the antibodies were not directed against the His tag sequence.

TABLE 4

| O.D. (sandwich ELISA) | PIIINP concentration according to Orion assay [ng/ml] | calculated PIIINP concentration based on sandwich ELISA calibrated by regression curve [ng/ml] |
|---|---|---|
| 0.543 | 2.6 | −1.9 |
| 0.794 | 5.3 | 5.5 |
| 0.761 | 7.0 | 4.5 |
| 1.210 | 11.1 | 17.7 |
| 1.328 | 16.7 | 22.0 |
| 1.190 | 21.9 | 17.1 |
| 1.692 | 29.6 | 31.8 |
| 1.773 | 36.8 | 34.2 |

Table 4 shows the results of PIIINP serum concentration measurements performed with the commercially available Orion assay and with the sandwich ELISA using the monoclonal antibody mAb 35J23 and polyclonal anti-PIIINP serum The assays are in excellent agreement (r=0.94). The third column depicts the calculated PIIINP concentration as estimated with the sandwich ELISA assay.

| Patient Child classification | calculated PIIINP concentration based on sandwich ELISA calibrated by regression curve [ng/ml] |
|---|---|
| A | below detection threshold |
| A | 2.5 |
| B | below detection threshold |

-continued

| Patient Child classification | calculated PIIINP concentration based on sandwich ELISA calibrated by regression curve [ng/ml] |
|---|---|
| B | 38.4 |
| B | 47.5 |
| C | below detection threshold |
| C | 28.4 |
| C | 35.7 |
| C | 42.1 |
| C | 44.2 |

Table 5 shows the results of PIIINP serum concentration measurements in sera from patients with fibrotic liver diseases. The patients were classified according to the clinical Child classification. Measurements were performed with the sandwich ELISA with the monoclonal antibody mAb 35J23 and polyclonal anti-PIIINP serum (Biodesign, U.K.). The assay was calibrated with sera where the PIIINP concentration was determined with the Orion RIA kit and the sandwich ELISA using the mAb 35J23 and polyclonal anti-PIIINP antiserum. The correlation between O.D.'s in the ELISA assay and the values from the Orion kit was excellent (r=0.76, data not shown here).

FIGURES

FIG. 1 shows the N-terminal cDNA sequence of preprocollagen (III) extending beyond the telomer region. The different primer locations described above are indicated by arrows pointing in the direction of polynucleotide chain extension.

FIG. 2 schematically shows the cDNA regions encoded by each of the constructs hP5, 4.5.2, 2.8.6, and clone6.

SEQUENCE LISTING

<160> NUMBER OF SEQ ID NOS: 13

Figure 1:
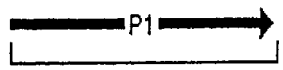
Figure 3:
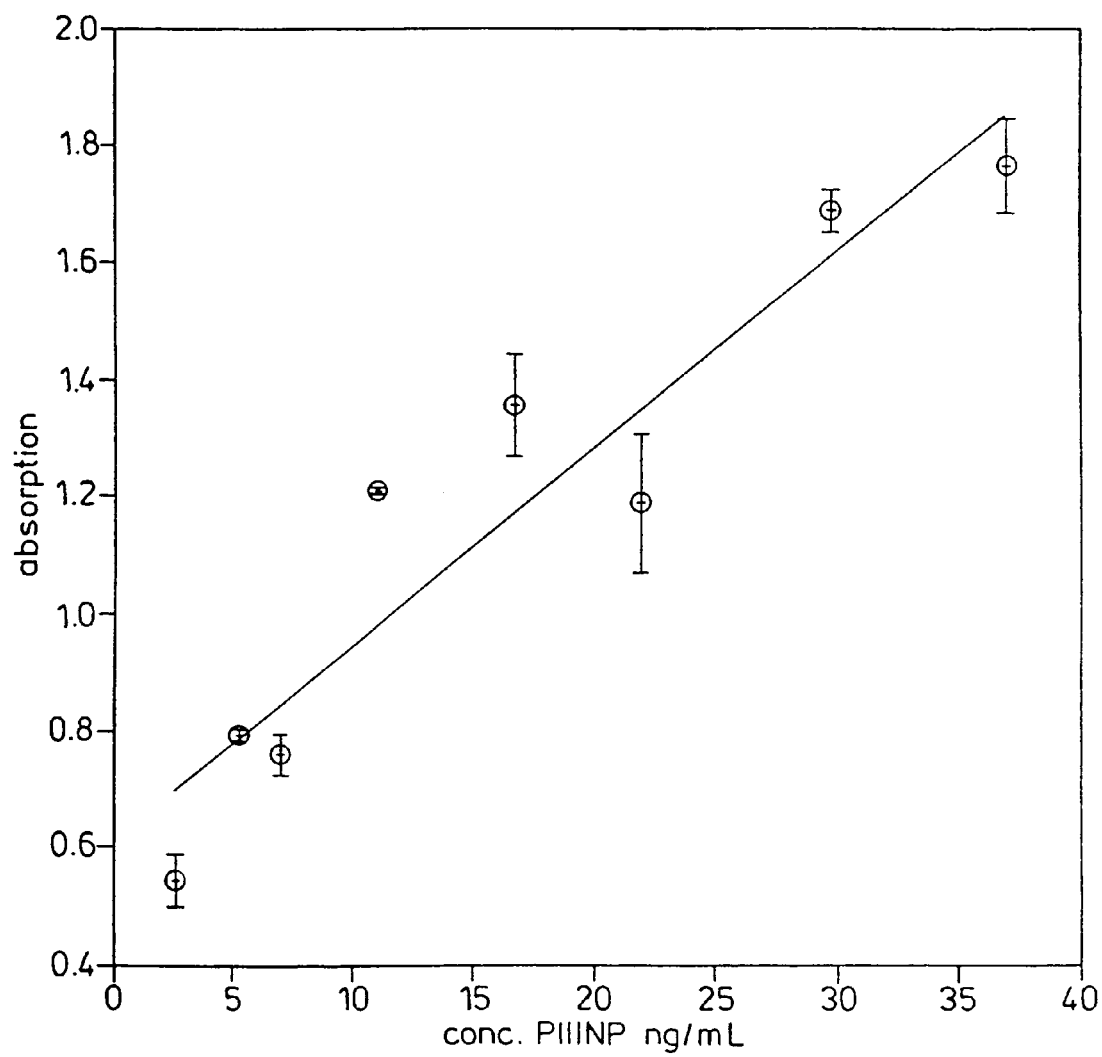
FIG. 3 shows the results of PIIINP serum concentration measurements performed with the commercially available Orion assay and their correlation with the results from the sandwich ELISA with the monoclonal antibody mAb 35J23 and polyclonal anti-PIIINP antiserum. The assays are in excellent agreement (r=0.94).
Figure 4:
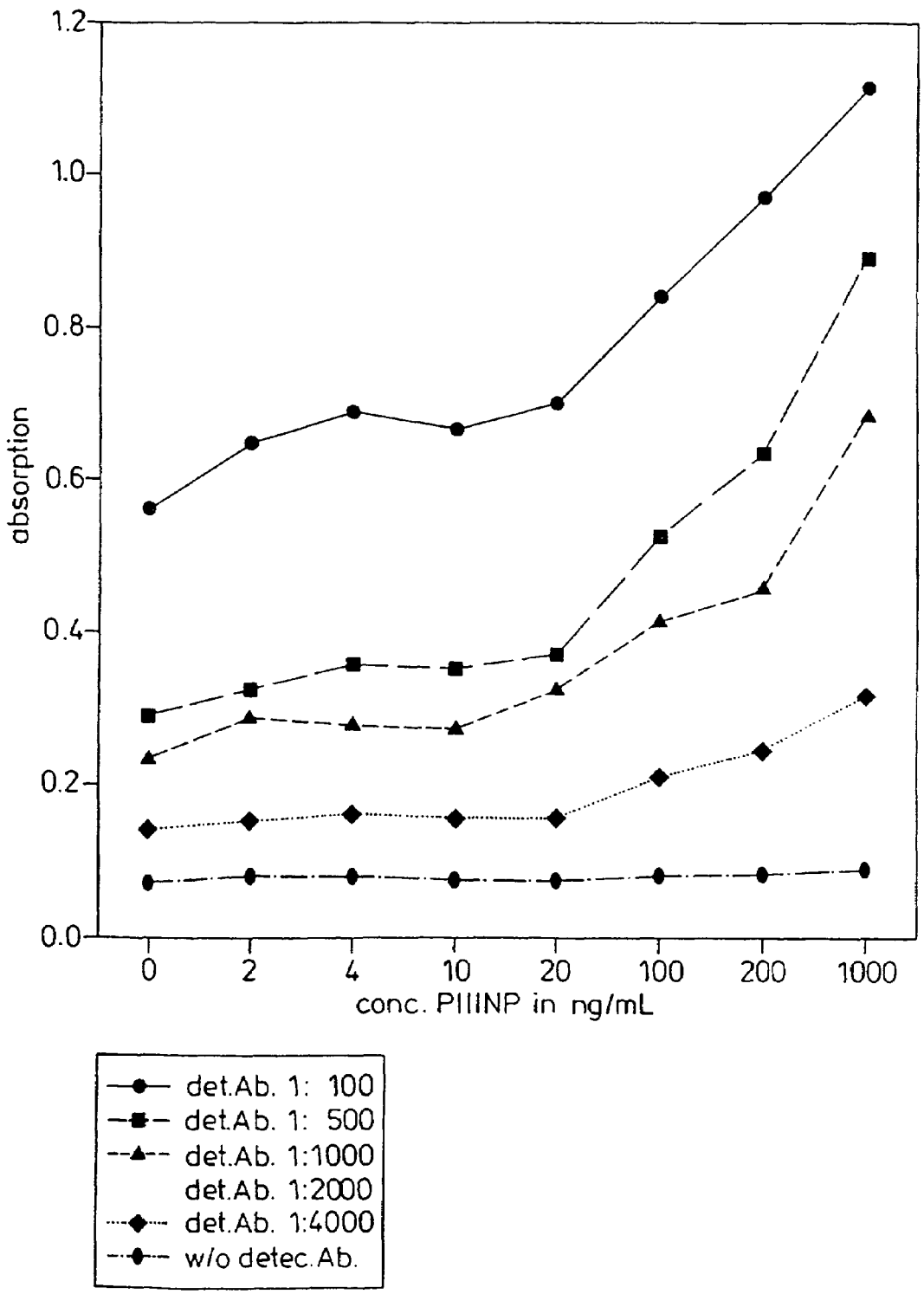
FIG. 4 shows the relationship between the absorptions measured with the sandwich ELISA assay with the monoclonal antibody mAb 35J23 in combination with polyclonal anti-PIIINP serum and the coating concentrations of recombinant monomeric PIIINP (4.5.2).

<210> SEQ ID NO 1
<211> LENGTH: 519
<212> TYPE: DNA
<213> ORGANISM: Primer

<400> SEQUENCE: 1
atgatgagct ttgtgcaaaa ggggagctgg ctacttctcg ctctgcttca tcccactatt      60
attttggcac aacaggaagc tgttgaagga ggatgttccc atcttggtca gtcctatgcg     120
gatagagatg tctggaagcc agaaccatgc caaatatgtg tctgtgactc aggatccgtt     180
ctctgcgatg acataatatg tgacgatcaa gaattagact gccccaaccc agaaattcca     240
tttggagaat gttgtgcagt ttgcccacag cctccaactg ctcctactcg ccctcctaat     300
ggtcaaggac ctcaaggccc caaggagat ccaggccctc ctggtattcc tgggagaaat      360
ggtgaccctg gtattccagg acaaccaggg tcccctggtt ctcctggccc ccctggaatc     420
tgtgaatcat gccctactgg tcctcagaac tattctcccc agtatgattc atatgatgtc     480
aagtctggag tagcagtagg aggactcgca ggctatcct                             519

<210> SEQ ID NO 2
<211> LENGTH: 173
<212> TYPE: PRT
<213> ORGANISM: Homo sapiens

<400> SEQUENCE: 2

Met Met Ser Phe Val Gln Lys Gly Ser Trp Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

-continued

```
Ile Ile Cys Asp Asp Gln Glu Leu Asp Cys Pro Asn Pro Glu Ile Pro
 65                  70                  75                  80

Phe Gly Glu Cys Cys Ala Val Cys Pro Gln Pro Pro Thr Ala Pro Thr
             85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro
                165                 170
```

<210> SEQ ID NO 3
<211> LENGTH: 31
<212> TYPE: DNA
<213> ORGANISM: Primer

<400> SEQUENCE: 3
cgcgggtacc aagggagct ggctacttct c                                 31

<210> SEQ ID NO 4
<211> LENGTH: 30
<212> TYPE: DNA
<213> ORGANISM: Primer

<400> SEQUENCE: 4
cgcgctgcag tgtgactcag gatccgttct                                  30

<210> SEQ ID NO 5
<211> LENGTH: 29
<212> TYPE: DNA
<213> ORGANISM: Primer

<400> SEQUENCE: 5
cgcgaagctt aggggaccct ggttgtcct                                   29

<210> SEQ ID NO 6
<211> LENGTH: 31
<212> TYPE: DNA
<213> ORGANISM: Primer

<400> SEQUENCE: 6
cgcgggtacc caggaagctg ttgaaggagg a                                31

<210> SEQ ID NO 7
<211> LENGTH: 31
<212> TYPE: DNA
<213> ORGANISM: Primer

<400> SEQUENCE: 7
cgcgaagctt aggatagcct gcgagtcctc c                                31

<210> SEQ ID NO 8
<211> LENGTH: 24
<212> TYPE: PRT
<213> ORGANISM: Homo sapiens

<400> SEQUENCE: 8

```
Met Arg Gly Ser His His His His His Gly Ser Ala Cys Glu Leu
1               5                   10                  15

Gly Thr Gln Glu Ala Val Glu Gly
            20

<210> SEQ ID NO 9
<211> LENGTH: 24
<212> TYPE: PRT
<213> ORGANISM: Homo sapiens

<400> SEQUENCE: 9

Met Arg Gly Ser His His His His His Gly Ser Ala Cys Glu Leu
1               5                   10                  15

Gly Thr Gln Glu Ala Val Glu Gly
            20

<210> SEQ ID NO 10
<211> LENGTH: 24
<212> TYPE: PRT
<213> ORGANISM: Homo sapiens

<400> SEQUENCE: 10

Met Arg Gly Ser His His His His His Gly Ser Ala Cys Glu Leu
1               5                   10                  15

Gly Thr Gln Glu Ala Val Glu Gly
            20

<210> SEQ ID NO 11
<211> LENGTH: 21
<212> TYPE: PRT
<213> ORGANISM: Homo sapiens

<400> SEQUENCE: 11

Gly Ser Pro Gly Pro Pro Gly Ile Cys Glu Ser Cys Pro Thr Gly Pro
1               5                   10                  15

Gln Asn Tyr Ser Pro
            20

<210> SEQ ID NO 12
<211> LENGTH: 14
<212> TYPE: PRT
<213> ORGANISM: Homo sapiens

<400> SEQUENCE: 12

Ile Cys Glu Ser Cys Pro Thr Gly Gly Gln Asn Tyr Ser Pro
1               5                   10

<210> SEQ ID NO 13
<211> LENGTH: 30
<212> TYPE: DNA
<213> ORGANISM: 'Axial Seamount' polynoid polychaete

<400> SEQUENCE: 13
cgcgaagctt gggagaatag ttctgaggac                                30
```

The invention claimed is:

1. A monoclonal antibody directed against an epitope within the 30 most N-terminal amino acids of the Col1 domain of human PIIINP, wherein the sequence of the 30 most N-terminal amino acids is Gln-Glu-Ala-Val-Glu-Gly-Gly-Cys-Ser-His-Leu-Gly-Gln-Ser-Tyr-Ala-Asp-Arg-Asp-Val-Trp-Lys-Pro-Glu-Pro-Cys-Gln-Ile-Cys-Val (amino acids 25 to 54 of SEQ ID NO 2).

2. The monoclonal antibody according to claim 1, wherein the antibody is characterized by preferentially binding to trimeric PIIINP as compared to monomeric col1 domain.

3. A monoclonal antibody produced from the mAb 35J22 cell line (ATCC PTA-9545).

4. A monoclonal antibody bound to a support; said monoclonal antibody being directed against an epitope within the 30 most N-terminal amino acids of the Col1 domain of human PIIINP, the sequence of the 30 most N-terminal amino acids being Gln-Glu-Ala-Val-Glu-Gly-Gly-Cys-Ser-His-Leu-Gly-Gln-Ser-Tyr-Ala-Asp-Arg-Asp-Val-Trp-Lys-Pro-Glu-Pro-Cys-Gln-Ile-Cys-Val (amino acids 25 to 54 of SEQ ID NO 2).

5. A monoclonal antibody produced from the mAb 35J22 cell line (ATCC PTA-9545) bound to a support.

\* \* \* \* \*